US011246563B2

(12) United States Patent
Van De Laar et al.

(10) Patent No.: US 11,246,563 B2
(45) Date of Patent: Feb. 15, 2022

(54) PREGNANCY MONITORING SYSTEM AND METHOD (71) Applicant: KONINKLIJKE PHILIPS N.V., Eindhoven (NL)

(72) Inventors: Jakob Van De Laar, Oosterhout (NL); Haris Duric, Bothell, WA (US); Lars Schmitt, Aachen (DE); Markus Wohlschlager, Sindelfingen (DE); Winfried Peter Kaiser, Wildberg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 875 days.

(21) Appl. No.: 15/033,120

(22) PCT Filed: Oct. 13, 2014

(86) PCT No.: PCT/EP2014/071835
§ 371 (c)(1),
(2) Date: Apr. 29, 2016

(87) PCT Pub. No.: WO2015/062851
PCT Pub. Date: May 7, 2015

(65) Prior Publication Data
US 2016/0256132 A1 Sep. 8, 2016

(30) Foreign Application Priority Data
Oct. 30, 2013 (EP) .................................... 13190860

(51) Int. Cl.
*A61B 8/08* (2006.01)
*A61B 5/00* (2006.01)
(Continued)

(52) U.S. Cl.
CPC ........ *A61B 8/0866* (2013.01); *A61B 5/02411* (2013.01); *A61B 5/1116* (2013.01);
(Continued)

(58) Field of Classification Search
CPC ....... A61B 8/0866; A61B 8/54; A61B 8/4227; A61B 8/4416; A61B 5/02411;
(Continued)

(56) References Cited

U.S. PATENT DOCUMENTS 5,817,035 A 10/1998 Sullivan
6,314,312 B1 11/2001 Wessels et al.
(Continued)

FOREIGN PATENT DOCUMENTS

| CN | 202589663 | 12/2012 |
|---|---|---|
| JP | 11-267124 | 10/1999 |
| JP | 2009039466 | 2/2009 |

*Primary Examiner* — Oommen Jacob
*Assistant Examiner* — Shahdeep Mohammed (57) ABSTRACT The present invention relates to a pregnancy monitoring system (10) and to a method for detecting medical condition information from a pregnant subject of interest (12). The system (10) comprises a fetal monitoring transducer (20) that detects fetal medical condition information, a first motion sensor unit (30) associated with the fetal monitoring transducer (20), the first motion sensor unit (30) comprising at least one first motion sensor (70, 72), a second motion sensor unit (32) comprising at least one second motion sensor (70, 72), and a control device (48) comprising an evaluation unit (50) that determines relative motion between the first motion sensor unit (30) and the second motion sensor unit (32), wherein the control device (48) selectively permits, in an enablement mode, processing of the detected fetal medical condition information when a level of relative motion between the first motion sensor unit (30) and the second motion sensor unit (32) indicates stable measurement conditions, and wherein the control device (48) selectively prevents, in a suppression mode, processing of the detected fetal medical condition information when the level of rela-
(Continued)

tive motion between the first motion sensor unit (30) and the second motion sensor unit (32) indicates unstable measurement conditions.

20 Claims, 6 Drawing Sheets

(51) Int. Cl.
  *A61B 5/11* (2006.01)
  *A61B 5/024* (2006.01)
  *A61B 8/00* (2006.01)
  *A61B 5/344* (2021.01)
(52) U.S. Cl.
  CPC ............ *A61B 5/344* (2021.01); *A61B 5/4362* (2013.01); *A61B 5/721* (2013.01); *A61B 8/4227* (2013.01); *A61B 8/4416* (2013.01); *A61B 8/54* (2013.01); *A61B 5/7221* (2013.01); *A61B 2503/02* (2013.01); *A61B 2562/0219* (2013.01)
(58) Field of Classification Search
  CPC ..... A61B 5/721; A61B 5/4362; A61B 5/1116; A61B 5/0444; A61B 2562/0219; A61B 2503/02
  See application file for complete search history.

(56) References Cited

U.S. PATENT DOCUMENTS

| | | |
|---|---|---|
| 6,751,498 B1 | 6/2004 | Greenberg |
| 2008/0154155 A1 | 6/2008 | Nishihara |
| 2008/0294022 A1 | 11/2008 | Barnev |
| 2009/0270767 A1 | 10/2009 | Nishihara |
| 2010/0168596 A1 | 7/2010 | Jaeschke et al. |
| 2010/0274145 A1 | 10/2010 | Tupin |
| 2011/0306893 A1 | 12/2011 | Harrold |
| 2012/0065479 A1* | 3/2012 | Lahiji ................ A61B 5/02411 600/301 |
| 2012/0123226 A1* | 5/2012 | Schwenk ............ A61B 5/1118 600/301 |
| 2012/0150010 A1 | 6/2012 | Hayes-Gill |
| 2013/0158366 A1* | 6/2013 | Bogineni ............ A61B 5/0002 600/301 |
| 2015/0150538 A1* | 6/2015 | Reuter ................ A61B 8/488 600/301 |

* cited by examiner

PREGNANCY MONITORING SYSTEM AND METHOD

CROSS REFERENCE TO RELATED APPLICATIONS

This application is the U.S. National Phase application under 35 U.S.C. § 371 of International Application No. PCT/EP2014/071835, filed Oct. 13, 2014, published as WO 2015/062851 on May 7, 2015, which claims the benefit of European Patent Application Number 13190860.0 filed Oct. 30, 2013. These applications are hereby incorporated by reference herein.

FIELD OF THE INVENTION

The present invention relates to a pregnancy monitoring system and to a method for detecting medical condition information from a pregnant subject of interest. More particularly, but not intended to limit the scope of the invention, the present disclosure relates to improvements in cardiotocography devices and methods used for monitoring a fetus in a pregnant woman.

The present invention further relates to a corresponding computer program.

BACKGROUND OF THE INVENTION

Pregnancy monitoring which may be also referred to as fetal monitoring and/or labor monitoring is commonly used in late stages of pregnancy. By way of example, during labor, physiological parameters such as fetal heart rate may be monitored so as to identify signs of fetal distress and/or fetal well-being. Prior to labor, the mother-to-be may undergo one or more medical ultrasound examinations, thereby providing fetal heart rate information, fetal movement information, fetal size information and similar information that is used to identify markers of fetal growth during pregnancy. During labor and birth, also uterine activity, particularly uterine contractions, may be monitored.

In gynecology and obstetrics, generally two medical parameters are important to assess the condition of the fetus. These two parameters are the fetal beat-to-beat heart rate, e.g. measured via an ultrasound Doppler signal, and uterus (or labor) activity. Simultaneous assessment of the fetal heart rate (FHR) and uterine activity allows an exact determination of the fetal condition. Monitoring systems that are capable of detecting both parameters are frequently referred to as cardiotocographs (CTG monitors). However, also fetal movement is considered as an indicative parameter for assessing the condition of the fetus. By way of example, a conventional CTG device (cardiotocography device) may contain an ultrasound Doppler transducer (US transducer) for measuring fetal heart rate (FHR) and detecting fetal movements, as well as a pressure transducer (also called toco transducer, or tocodynamometer) for measuring uterine activity. Each of the transducers may be placed on the abdomen of the mother, e.g. by an elastic belt fitted around the waist or by an adhesive tape or patch. Each of the transducers may be mounted inside a respective probe. Particularly the ultrasound transducer may be manually placed and positioned so as to seek for a considerably strong signal, e.g. a considerably strong heart beat or heart rate signal. An ideal position of the ultrasound transducer at the expectant mother's abdomen may depend on an actual orientation of the fetus.

It has been observed that motion of the fetal movement transducers, e.g., due to (re)positioning of the transducer and/or due to maternal movement may cause the ultrasound transducer to falsely indicate fetal movement. As a result, fetal movement detections are usually only reliable when there are no motion artifacts.

In this context, US 2012/0150010 A1 discloses an apparatus for detecting uterine activity, the apparatus comprising first input means configured to receive electrical signals from cutaneous electrodes, second input means configured to receive movement signals indicative of a movement of the maternal body from a movement detector; signal processing means configured to separate a uterine electromyogram signal from fetal and maternal heart rate signals in the electrical signals and to filter maternal motion artifacts from the uterine electromyogram using the movement signals, and output means configured to present electrohysterogram data from the uterine electromyogram signal.

The document further discloses several refinements of the apparatus and a related method. Particularly, the document proposes to filter maternal motion artifacts from the electromyogram signal by attenuating the electromyogram signal as a function of the magnitude of the movement signals. Also the detection of fetal heart rate is addressed.

US 2009/0270767 A1 discloses a fetal movement information processing device and method for predicting the healthy development state of a fetus, the device comprising a fetal movement signal collecting device including at least one fetal movement sensor attached to a pregnant woman's abdomen for detecting fetal movements; and a fetal movement detected information storage means for storing fetal movement detection signals detected by said fetal movement sensor in association with detection time information; a fetal movement information processing means for calculating fetal movement amounts per time unit for each pregnancy week from maternal information identifying the pregnant woman and number of pregnancy days information, along with the fetal movement detection signals and the detection time information stored in the fetal movement detected information storage means of said fetal movement signal collecting device; and a display/output means capable of arranging and displaying fetal movement amounts obtained.

In prior art cardiotocography methods and devices, maternal movement can be measured with a maternal movement sensor attached to the mother's abdomen. The signals provided by such kind of sensors can be used for the detection of maternal movement and for subsequent suppression of the fetal movement (ultrasound) transducer's output signals or parameters derived therefrom.

It has been observed that also these improved devices still may be vulnerable to falsely determined attenuation phases resulting in overall measurement errors. This is at least in part attributable to a variety of potential undesired motion-related effects that may occur during pregnancy monitoring sessions.

SUMMARY OF THE INVENTION

It is an object of the present invention to provide for a pregnancy monitoring system and a related method that may allow for an improved monitoring accuracy. It would be further advantageous to provide for a system and a method that are less susceptible to motion-related mismeasurements. Preferably, the system and method are suitably arranged for enabling reliable measurements also under motion-afflicted monitoring conditions. Even more preferably, the system and the method are capable of processing types of disturbances and/or errors that generally cannot be handled well by conventional systems.

In a first aspect of the present invention a pregnancy monitoring system is presented, the system comprising:
- a fetal monitoring transducer that detects fetal medical condition information;
- a first motion sensor unit associated with the fetal monitoring transducer, the first motion sensor unit comprising at least one first motion sensor;
- a second motion sensor unit comprising at least one second motion sensor;
- a control device comprising an evaluation unit that determines relative motion between the first motion sensor unit and the second motion sensor unit, wherein the determination of relative motion is based on motion signals supplied by the at least one first motion sensor and the at least one second motion sensor;
- wherein at least one of the at least one first motion sensor and the at least one second motion sensor is attachable to an abdominal region of a subject of interest;
- wherein the control device selectively permits, in an enablement mode, processing of the detected fetal medical condition information when a level of relative motion between the first motion sensor unit and the second motion sensor unit indicates stable measurement conditions; and
- wherein the control device selectively prevents, in a suppression mode, processing of the detected fetal medical condition information when the level of relative motion between the first motion sensor unit and the second motion sensor unit indicates unstable measurement conditions.

This aspect is based on the insight that, in addition to the fetal monitoring transducer, at least two distinct motion sensors may be applied to allow for considerable improvements in signal quality and measurement accuracy. At least one of the motion sensors, particularly the at least one second motion sensor, may serve as a reference sensor. The reference sensor and the respective sensor unit may provide a reference motion and/or location signal.

Consequently, motion and/or location signals delivered by the at least one first sensor and the at least one second sensor may be processed such that a first motion signal and a second motion signal may be acquired. By comparing the first motion signal with the second motion signal, at least one relative motion signal can be generated. One or more of the motion signals can be assessed by the control device so as to eventually define whether or not the actually detected or detectable fetal medical condition information may be regarded as reliable information. Based on the decision made by the control device, further processing of the detected fetal medical condition information may be permitted or prevented. Permitting may include passing and/or transferring the signals comprising the desired information. Preventing may include attenuating and/or omitting the signals comprising the desired information. Preventing and/or permitting information processing may be applied on a temporary basis.

The signal basis for the motion determination may be extended by adding at least a further motion signal channel, i.e. provided by the at least one second motion sensor. Extending the signal basis for the determination of undesired motion influences may significantly improve monitoring accuracy and reliability. In other words, prior art devices and systems relying on a single motion sensor in addition to a fetal monitoring transducer, for instance, have limited capability of motion detection, and thus frequently monitoring accuracy is impaired since it is not unlikely that disturbed signals may be transferred for further processing and, in some cases, even plain signals that are not motion-affected are erroneously attenuated.

The at least one first motion sensor, being associated with the fetal monitoring transducer, may have a basically predefined orientation and location with respect to the fetal monitoring transducer, at least when in contact with the abdominal region. In other words, the fetal monitoring transducer and the at least one first motion sensor may undergo basically the same or, at least, similar (absolute) movements. In other words, it may be preferred in some embodiments that relative motion between the at least one first motion sensor and the fetal monitoring transducer is generally prevented, at least in part.

The at least one second motion sensor, generally not being associated with the fetal monitoring transducer, may experience motion in a manner basically independent of the fetal monitoring transducer. Therefore, relative motion between the at least one second motion sensor and the fetal monitoring transducer is basically allowed. Relative motion between the at least one second motion sensor and the at least one first motion sensor may therefore be regarded as a measure for relative motion between the at least one second motion sensor and the fetal monitoring transducer. Having knowledge of this measure basically allows for enhanced signal classification under consideration of actual motion influences.

Furthermore, also the detection of actual posture-related signals can be enhanced in this way since the at least one first motion sensor and the at least one second motion sensor may be subjected to relative motion with respect to each other. Changes in the relative position of the at least one first motion sensor and the at least one second motion sensor may be analyzed such that posture-related (or: posture) information may be inferred from that, provided that the at least one first motion sensor and the at least one second motion sensor are applied to or attached to a posture changing subject of interest.

Preferably, the at least one first motion sensor and the at least one second motion sensor are spaced apart from each other when applied to the subject of interest. It may be preferred that the at least one first motion sensor and the at least one second motion sensor are spaced apart, when being applied to the subject during monitoring, by a distance of at least 0.1 m (meter), preferably of at least 0.15 m, more preferably of at least 0.25 m at the abdominal portion of the subject.

As used herein, the term medical condition information may generally involve medical condition indicative information. In connection with the embodiment relating to cardiotocography, fetal heart rate, fetal movement, uterine contractions, etc., and related information may be regarded as medical condition information.

As used herein the term motion may also generally relate to the term movement. Any type of movement and/or motion with respect to a fixed local world reference system shall be referred to when using the term motion. Furthermore the term motion may include absolute motion and/or relative motion. Motion may generally involve movements consisting of translation, rotation (which can be interpreted as orientation change), or a combination thereof. Each motion sensor unit may be formed by at least one distinct motion sensor. It may be further preferred that at least one of the first motion sensor unit and the second motion sensor unit comprises more than one respective motion sensor, particularly two or more sensors.

It is worth to be mentioned in this connection that at least in some embodiments, the at least one first motion sensor and the at least one second motion sensor should not be mixed up with sensors that detect medical condition information, for instance, the fetal monitoring transducer. Although it is acknowledged that also the fetal monitoring transducer and, in some embodiments, a respective maternal monitoring transducer (as set out below) may detect signals that are motion-related, such as, for instance, fetal heart rate and/or uterine contractions, it is emphasized that the at least one first motion sensor and the at least one second motion sensor may be regarded as separate specialized motion sensors. In other words, at least in some embodiments, the at least one first motion sensor and the at least one second motion sensor may be embodied by single-purpose motion sensors, such as, for instance, by accelerometers, gyroscope sensors, inertial measurement units, etc.

A motion sensor may be regarded as a sensor that is capable of detecting motion along at least one axis. Motion in an exemplary (e.g., Cartesian) reference space may comprise six degrees of motion, wherein three degrees of linear motion along respective axes may be present (e.g., X-axis, Y-axis, and Z-axis), and wherein three degrees of rotational motion about the respective axes may be present. An exemplary resulting three-dimensional motion path or track specified in a multidimensional space may be composed of respective motion components attributable to rectilinear motion and/or rotational motion with respect to a respective axis. The motion sensor may be adapted to detect motion with respect to at least one of the six degrees of motion.

Particularly in connection with fetal monitoring, it may be fairly assumed that in the future unobtrusive monitoring will be performed making use of wireless transducers enabling a pregnant woman to enjoy some freedom of movement, for instance, to walk around. On the downside, false fetal movement indications may be expected in this regard. A system for measuring fetal movements may comprise at least one additional motion sensor, preferably two additional motion sensors. Depending on respective detected motion parameters, fetal medical condition information may be suppressed.

According to an embodiment of the monitoring system a maternal monitoring transducer is provided that detects maternal medical condition information, wherein the second motion sensor unit is associated with the maternal monitoring transducer. Consequently, the control device may also selectively permit or prevent processing of the detected maternal medical condition information, in an enablement mode, and in a suppression mode, respectively. Detecting maternal medical condition information may further enhance the application range of the pregnancy monitoring system. It is particularly beneficial to detect both fetal and maternal medical condition information. A comprehensive patient supervision during pregnancy stages and/or birth may be enabled in this way.

However, several alternative embodiments may be envisaged in which the at least one second motion sensor (or: the second motion sensor unit) is not associated with any medical information monitoring transducer. In other words, the at least one second motion sensor may also be regarded as a separate motion sensor that is applied to or attached to the to-be-monitored subject, e.g. to an abdominal region of a pregnant mother-to-be. Also in this way the at least one second motion sensor may provide reference motion data that may be used to detect and evaluate motion appearances.

The at least one second motion sensor, at least in some embodiments, being associated with the maternal monitoring transducer, may have a basically predefined orientation and location with respect to the fetal monitoring transducer, at least when in contact with the abdominal region. In other words, the fetal monitoring transducer and the at least one first motion sensor may undergo basically the same or, at least, similar (absolute) movements. Put differently, it may be preferred in some embodiments that relative motion between the at least one first motion sensor and the fetal monitoring transducer is generally prevented, at least in part.

Optionally, particularly in cases where more than two motion sensor units are available, a motion sensor unit may be associated with the fetal monitoring transducer, another motion sensor unit may be associated with the maternal monitoring transducer, and yet another motion sensor unit may be applied to the abdominal region of the pregnant mother-to-be as a basically independent motion sensor unit. Consequently, at least three motion sensors may be arranged so as to acquire motion data in addition to the medical condition information detectable though the fetal monitoring transducer and the maternal monitoring transducer.

According to yet another embodiment, the fetal monitoring transducer is configured as an ultrasonic transducer that detects fetal heart rate indicative or fetal movement indicative information. According to still another embodiment, the maternal monitoring transducer is a pressure sensitive transducer that detects maternal uterine activity indicative information. In some embodiments, the maternal monitoring transducer may be configured as a uterine contraction transducer, which may also be referred to as tocodynamometer, and the fetal monitoring transducer may be configured as a fetal heart rate transducer, which may also be referred to as ultrasonic sensor.

Whenever motion of or relative motion between the at least one first motion sensor and the at least one second motion sensor is detected, a respective classification of the motion occurrences may be performed. For instance, incorrect operation, unintentional displacements, posture changes, and further motion patterns may be detected. Consequently, signal processing and/or signal transmission may be controlled accordingly while classification errors may be reduced to the enhanced motion signal space.

In another embodiment, at least one of the at least one first motion sensor and the at least one second motion sensor is an accelerometer sensor that detects acceleration indicative information. Alternatively, the at least one first motion sensor and the at least one second motion sensor may be embodied by a respective gyroscope sensor or an inertial measurement sensor, such as an inertial measurement unit. It is generally emphasized that the at least one first motion sensor and the at least one second motion sensor are preferably separate from and/or distinct of any of the fetal monitoring transducer and the maternal monitoring transducer while, in some embodiments, still being associated with and/or connected to the fetal monitoring transducer and the maternal monitoring transducer.

In conventional accelerometer sensors, commonly piezoelectric, piezo-resistive and/or capacitive components are used to convert (mechanical) motion into a signal. Many accelerometer sensors are designed to be sensitive only to a direction. It is therefore not uncommon to combine several accelerometer sensors having different orientations so as to define a motion sensor that is capable of detecting multi channel (or: multi axis) motion in a reference system having two or more (typically up to six) degrees of motion. However, accelerometers, or, more generally, motion sensors as such, that are sensitive in more than one direction may be implemented as well. For instance, respective micro-electromechanical systems, gyroscopes, and inertial measurement units may be used to this end.

In yet another embodiment, the fetal monitoring transducer and the first motion sensor unit are mechanically linked to each other. For instance, the fetal monitoring transducer and the first motion sensor unit are integrated in a common housing and or attached to a common strap or adhesive tape or strap. Accordingly, It may be further preferred, at least in some embodiments, that the maternal monitoring transducer and the second motion sensor unit are mechanically linked to each other.

In still another embodiment, the first motion sensor unit and the second motion sensor may be attachable, independently of each other, to the abdominal region of the subject of interest. It is preferred in some embodiments that no mechanical link exists between the first motion sensor unit and the second motion sensor such that relative motion between the first motion sensor unit and the second motion sensor may be allowed without huge resistance.

According to another embodiment, the control device is further configured for selectively suspending, in a suspension mode, processing of the detected fetal medical condition information after detecting a movement pattern indicating unstable measurement conditions. As used herein, the term "unstable measurement conditions" may particularly refer to a change in posture of the subject of interest. However, also other kinds of fault causes and effects as already set out above can be regarded as unstable measurement conditions in this context. This aspect may also apply to the maternal medical condition information, at least in some embodiments. It is preferred in this connection that the control device is capable of evaluating motion signals provided by the at least one first motion sensor and the at least one second motion sensor, particularly evaluating relative motion signals. The control device may comprise or may be coupled to a data base where a posture model and/or a posture change model may be stored. Actual motion and/or orientation change patterns may be compared with respective (pre)defined posture and/or posture change patterns. A respective suspension period may be generally referred to as guard interval.

It has been observed, in connection with some embodiments, that a (significant) maternal posture change might induce a movement or orientation change of the fetus as a whole with respect to the maternal body. This latter process might take longer than the subject's actual posture change. When the posture change starts this is detected as motion by the motion sensors and fetal movement indication may be suppressed, for instance. However, when a new posture has been reached, the motion sensors do not detect motion anymore and thus often fetal medical information indication is no longer suppressed. This might lead to fetal movement detections and indications that are not caused by actual movements of the fetus itself, but rather by its relative motion as a whole with respect to the maternal body. Applying a (temporal) guard interval may be beneficial since in this way the fetus may come to rest before the fetal medical information may be reassumed. Basically the same may apply to the maternal medical information.

Correspondingly, according to another embodiment, the evaluation unit may further determine, on the basis of the motion determination, overall orientation information, wherein the evaluation unit further determines a change in posture of the subject of interest indicated by a change in overall orientation of the subject of interest. The change in overall orientation may comprise, for instance, tossing and turning in bed.

This embodiment may be further developed in that the evaluation unit is further configured to determine overall orientation information indicated by relative motion between at least two of the at least one first motion sensor and the at least one second motion sensor. This may basically involve that the evaluation unit is further capable of determining a movement pattern for at least one of the at least one first motion sensor and the at least one second motion sensor, the movement pattern including motion and orientation information.

According to a further developed embodiment, the control device selectively permits, in the enablement mode, processing of the overall orientation information when a level of relative motion between the first motion sensor unit and the second motion sensor unit indicates stable measurement conditions, and wherein the control device selectively prevents, in the suppression mode, processing of the overall orientation information when the level of relative motion between the first motion sensor unit and the second motion sensor unit indicates unstable measurement conditions. This embodiment is based on the insight that also the overall orientation information may be corrupted due to undesired displacements and/or compressive stress.

As used herein, in some embodiments, processing of the overall orientation information may relate to the determination of the overall orientation information. However, in some embodiments, processing of the overall orientation information may relate to transferring the (determined) overall orientation information, e.g. for further processing and evaluating. In other words, the determination of the overall orientation information may be continued even in cases where unstable measurement conditions are detected, wherein, at the same time, the detected fetal medical information is withheld from being further processed.

In another aspect of the present invention a method for detecting medical condition information from a pregnant subject of interest is presented, the method comprising the steps of:

providing a fetal monitoring transducer that detects fetal medical condition information;
  providing a first motion sensor unit associated with the fetal monitoring transducer, the first motion sensor unit comprising at least one first motion sensor;
  providing a second motion sensor unit comprising at least one second motion sensor;
  determining relative motion between the first motion sensor unit and the second motion sensor unit, wherein the determination of relative motion is based on motion signals supplied by the at least one first motion sensor and the at least one second motion sensor;
  permitting, in an enablement mode, processing of the detected fetal medical condition information when a level of relative motion between the first motion sensor unit and the second motion sensor unit indicates stable measurement conditions; and
  preventing, in a suppression mode, processing of the detected fetal medical condition information when the level of relative motion between the first motion sensor unit and the second motion sensor unit indicates unstable measurement conditions.

The method may be carried out using the system of the present disclosure. Needless to say, the method may be used in a continuous monitoring process. Of course, also spot check monitoring is possible.

According to a further embodiment of the method in accordance with the present disclosure, the method may further comprise the steps of:

providing a maternal monitoring transducer that detects maternal medical condition information, wherein the second motion sensor unit is associated with the maternal monitoring transducer; and applying the at least one first motion sensor and the at least one second motion sensor to an abdominal region of a subject of interest.

According to yet another embodiment of the method in accordance with the present disclosure, the method may further comprise the steps of:

determining, on the basis of the motion determination, overall orientation information;

permitting, in the enablement mode, processing of the overall orientation information when a level of relative motion between the first motion sensor unit and the second motion sensor unit indicates stable measurement conditions;

preventing, in the suppression mode, processing of the overall orientation information when the level of relative motion between the first motion sensor unit and the second motion sensor unit indicates unstable measurement conditions;

determining a change in posture of the subject of interest indicated by a change in overall orientation of the subject of interest detected in the enablement mode; and suspending, in a suspension mode, processing of the detected fetal medical condition information in response to a detection of a movement pattern indicating a change in posture of the subject of interest.

In yet another aspect of the present invention, there is provided a computer program which comprises program code means for causing a computer to perform the steps of the method in accordance with the present disclosure when said computer program is carried out on that computer. As used herein, the term "computer" may stand for a large variety of processing devices. In other words, also mobile devices having a considerable computing capacity can be referred to as computing device, even though they provide less processing power resources than standard "computers". Needless to say, such a "computer" can be a part of a medical device and/or system. Furthermore, the term "computer" may also refer to a distributed computing device which may involve or make use of computing capacity provided in a cloud environment. The term "computer" may also relate to medical technology devices, fitness equipment devices, and monitoring devices in general, that are capable of processing data. Preferred embodiments of the disclosure are defined in the dependent claims. It should be understood that the claimed method and the claimed computer program can have similar preferred embodiments as the claimed device and as defined in the dependent device claims.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

In the following, several embodiments of systems and method that can make use of at least some aspects of the present disclosure will be presented and elucidated in more detail.

Figure 1:
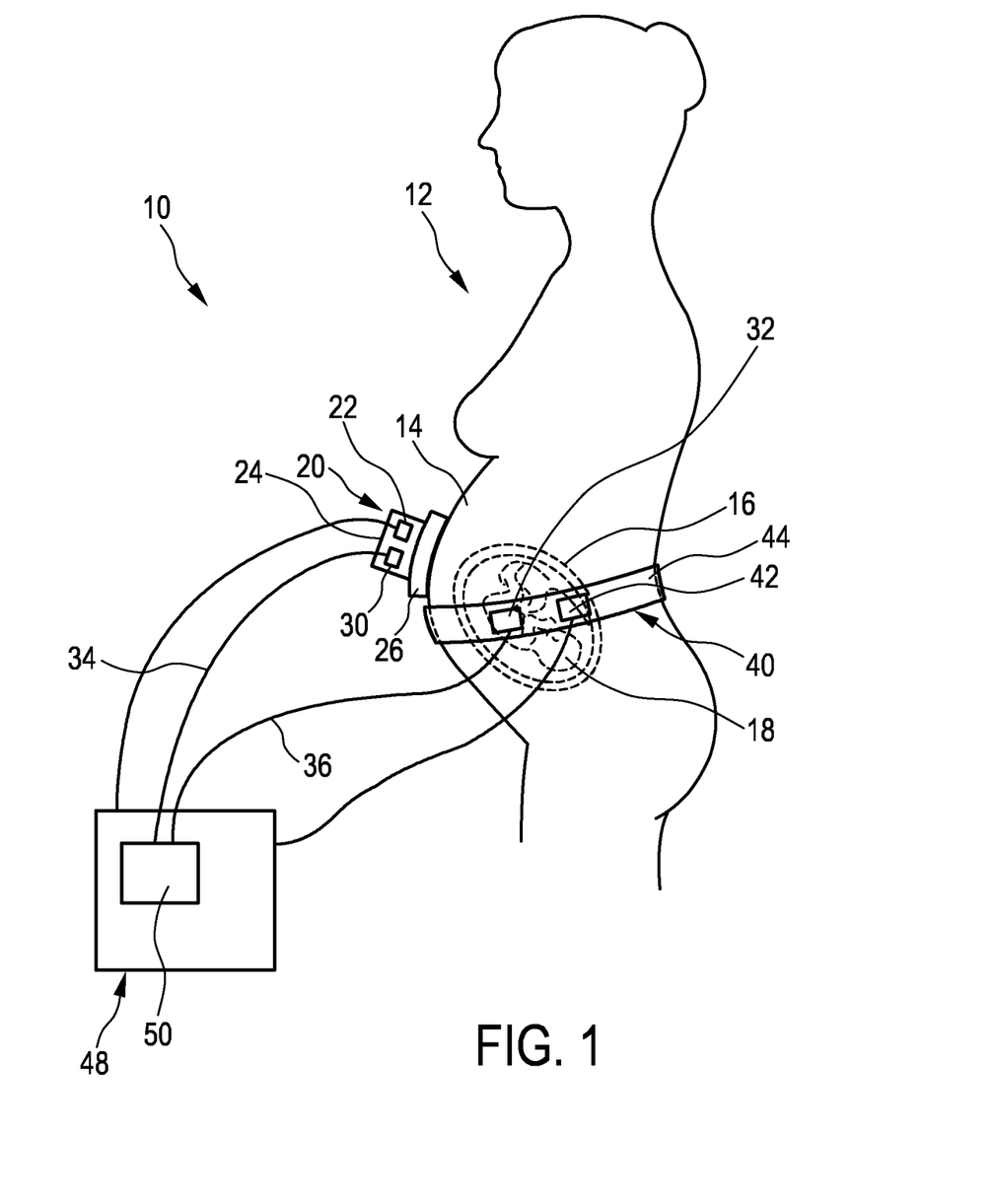
FIG. 1 shows a simplified schematic illustration of a monitoring system according to an embodiment of the present disclosure.

By way of example, FIG. 1 shows a pregnancy monitoring system 10 for monitoring a fetus 18 in a womb or uterus 16 of a to-be-monitored subject 12, particularly a pregnant female subject. Generally, the system 10 may be applied to an abdominal portion 14 of the subject 12. The system 10 may be capable of monitoring fetal medical condition information, such as fetal motion or, more precisely, fetal heart rate indicative signals. The system may be further capable of monitoring the subject 12, thereby obtaining maternal medical condition information, such as, for instance, uterine contractions.

The system 10 comprises a fetal monitoring transducer 20. The fetal monitoring transducer 20 may be regarded as a fetal heart rate transducer, for instance. Commonly, the fetal monitoring transducer 20 comprises at least one ultrasound sensor 22 that is capable of non-invasively detection fetal.

In some applications, the fetal monitoring transducer 20 may be manually guided and moved along the abdominal portion 14 of the subject 12 by an operator in order to find a strong fetal signal. It goes without saying that also any displacement of the fetal monitoring transducer 20 at the abdomen may be somehow reflected by a signal provided by the ultrasound sensor 22. Consequently, a desired fetal signal may be strongly distorted.

The fetal monitoring transducer 20 may further comprise a housing 24 to which a contact face or pad 26 may be attached. The pad 26 may be configured for contacting the abdominal skin of the subject 12 during operation. The ultrasound sensor 22 may be embedded in the housing 24. Further, at least one first motion sensor unit 30 may be associated with the fetal monitoring transducer 20. Particularly, the at least one first motion sensor unit 30 may be provided in the housing 24 as well. Consequently, the ultrasound sensor 22 and the at least one first motion sensor unit 30 may experience basically similar motion occurrences.

The system 10 may further comprise at least one second motion sensor unit 32. The at least one second motion sensor unit 32 may serve as a reference motion sensor unit 32 for the first motion sensor unit 30. The first motion sensor unit 30, the second motion sensor unit 32 and, if also provided, any further motion sensor unit may be connected to a control device 48 comprising an evaluation unit 50 via respective signal connectors 34, 36 e.g. via wire-based or wireless signal lines.

In some embodiments, the at least one second motion sensor unit 32 may be associated with a maternal monitoring transducer 40 that is capable of detecting maternal medical condition information. For instance, the maternal monitoring transducer 40 may comprise at least one tocodynamometer transducer 42 that is capable of detecting uterine contractions. Generally, the maternal monitoring transducer 40 may be connected to a respective attachment element 44, such as, for instance, a strap that may be attached to the abdominal region 14 of the subject 12. It may be preferred that the at least one second motion sensor unit 32 is associated with the maternal monitoring transducer 40. By way of example, the at least one second motion sensor unit 32 and the maternal monitoring transducer 40 may be integrated into a common housing (not shown in FIG. 1). It is generally preferred that also maternal monitoring transducer 40, particularly the tocodynamometer transducer 42 thereof and the at least one second motion sensor unit 32 are arranged close to each other and, preferably mechanically linked to each other, such that they experience basically similar motion occurrences.

Figure 2:
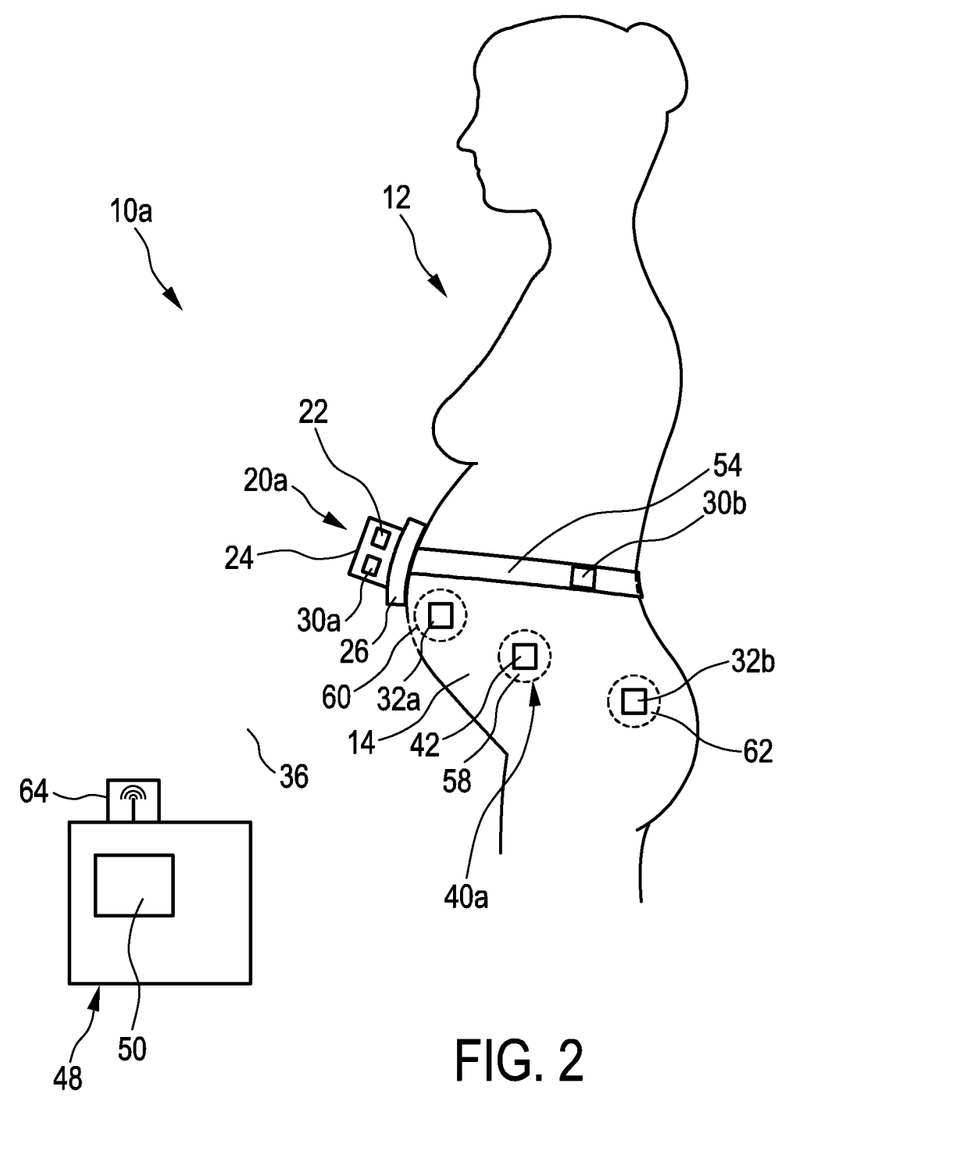
FIG. 2 shows a simplified schematic illustration of another monitoring system according to an embodiment of the present disclosure.

FIG. 2 shows an alternative layout of a pregnancy monitoring system 10a. As can be seen in FIG. 2, a fetal monitoring transducer 20a may be provided that may basically correspond to the fetal monitoring transducer 20 illustrated in connection with FIG. 1. The fetal monitoring transducer 20a comprises a first motion sensor unit that is composed of two or more components 30a, 30b, e.g. distinct sensors, that are spaced apart from each other. By way of example, the motion sensor unit component 30a may be integrated into the housing 24 while the motion sensor unit component 30b may be attached to an attachment element or strap 54.

As can be further seen from the at least one second motion sensor unit 32a, 32b does not necessarily have to be mechanically linked to maternal monitoring transducer 40a and the tocodynamometer transducer 42, respectively. As already indicated above, also the second motion sensor unit may be composed of two or more components 32a, 32b. In some embodiments, the tocodynamometer transducer 42 and the components 32a, 32b of the second motion sensor unit may be coupled to respective attachment elements 58, 60, 62. The attachment elements 58, 60, 62 generally may be embodied by straps, adhesive strips, patches, suction caps, for instance. As can be also seen in FIG. 2, indicated by a reference number 64 designating a wireless communication module, medical condition information and motion information may be transferred wirelessly.

Figure 3:
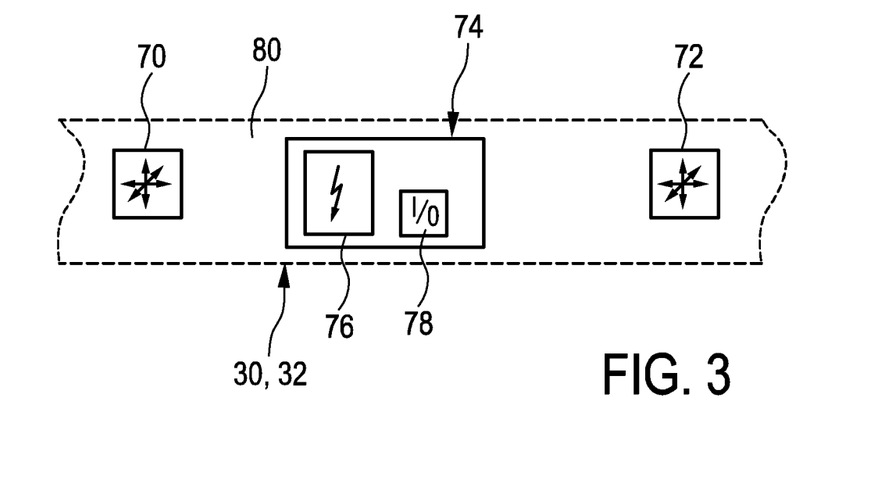
FIG. 3 shows a simplified schematic illustration of a layout of a motion sensor unit in accordance with an embodiment of the present disclosure.

FIG. 3 shows a simplified layout of a motion sensor unit 30, 32 that may generally serve as a motion sensor unit that can be associated with the fetal monitoring transducer 20 and/or the maternal monitoring transducer 40. The motion sensor unit 30, 32 may be composed of at least one motion sensor 70, 72. Each of the at least one motion sensor 70, 72 may be configured as accelerometer-based motion sensor, for instance. The motion sensor unit 30, 32 may further comprise a controller unit 74 that may be provided with a controller 76 and an input/output port 78. At least some or each of the components 70, 72, 74 may be arranged on a carrier strap 80, or in a respective housing or in another suitable way. It shall be understood that those skilled in the art may readily identify, deduce and implement similar motion sensor units 30, 32 that may be coupled to the monitoring systems 10, 10a so as to further improve monitoring accuracy and reliability.

Figure 4:
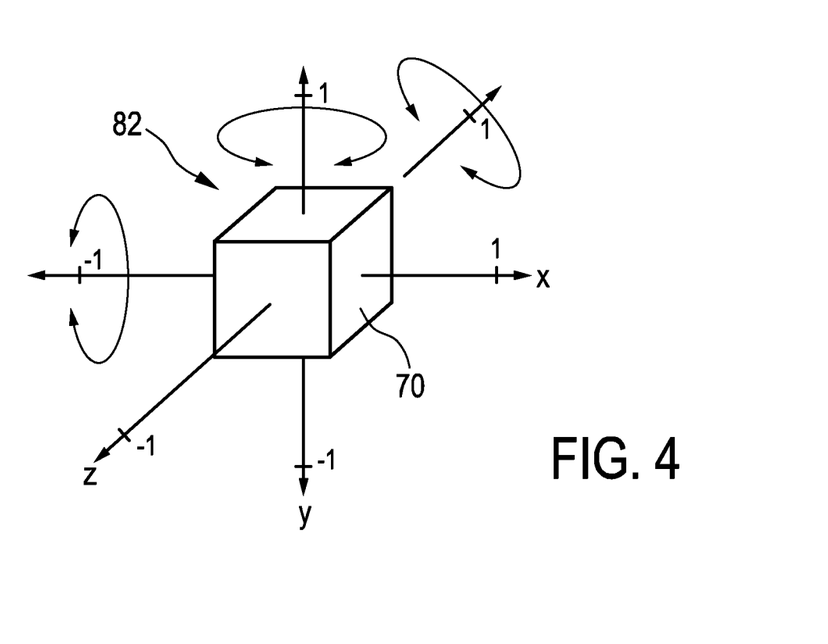
FIG. 4 shows a simplified representation of a coordinate system illustrating posture/orientation classification approaches.

FIG. 4 shows a simplified representation of a coordinate system 82 that may illustrate exemplary approaches to posture detection, or, more generally, orientation detection making use of at least one motion sensors. It is worth to be mentioned in this context that a motion sensor which may be implemented in the system set out above may be regarded as an accelerometer, or another suitable sensor that is capable of detecting motion, that comprises at least one motion sensing element.

Generally, posture detection can be performed by detecting actual motion and/orientation vectors that can be compared with reference vectors indicating reference postures. Posture detection may include the evaluation of signals that are provided from at least a single motion sensor. Posture detection may include the evaluation of signals that are provided from a plurality of motion sensors. The following table exemplifies a predefined set of postures and respective (unit) vectors, primarily for illustrative purposes.

| Posture # | Reference vector [x y z] | Posture name |
|---|---|---|
| 1 | [0, 0, 1] | Supine |
| 2 | [0, 1, 1]/√2 | Reclined |
| 3 | [0, 1, 0] | Upright |
| 4 | [0, 1, −1]/√2 | Forward |
| 5 | [0, 0, −1] | Prone |
| 6 | [0, −1, 0] | Upside down |
| 7 | [−1, 0, 0] | Left side |
| 8 | [1, 0, 0] | Right side |

Posture detection processes may generally consist of at least some of the following steps:
  Averaging accelerometer observations over a certain time span, e.g. of 1 second;
  Normalizing the resulting vector to have unit length;
  Calculating three dimensional Euclidean distances between the normalized vector on the one hand and all predefined reference vectors on the other hand;
  Detecting the reference posture vector that has the smallest distance/deviation to the normalized vector; and
  Providing the posture corresponding to the reference posture vector found in the previous step as being the actual posture.

It is emphasized that those skilled in the art may readily identify, deduce and apply similar motion and posture detection devices and approaches.

Figure 5:
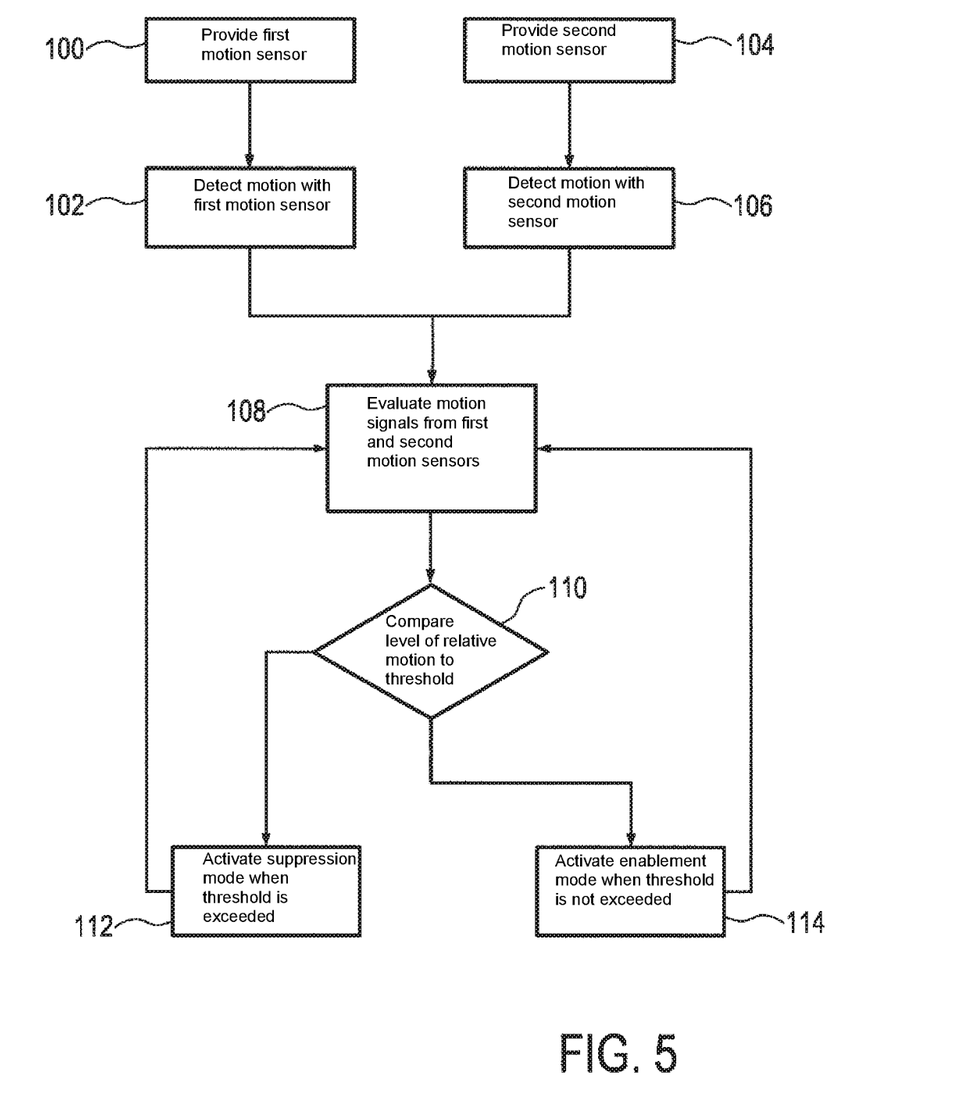
FIG. 5 shows an illustrative block diagram representing several steps of an embodiment of a method in accordance with the present disclosure.

Reference is made to FIG. 5 schematically illustrating a method for determining a motion level in a monitoring system for an observed subject, particularly a pregnant subject. At a first step 100, a first motion sensor unit may be provided, the first motion sensor unit comprising at least one first motion sensor. Preferably the at least one first motion sensor is associated with, particularly mechanically linked to a first (or: fetal monitoring) transducer. The at least one first motion sensor may be applied to an abdominal region of the pregnant subject. The at least one first motion sensor may be associated with at least one fetal monitoring transducer that detects fetal medical condition information. At a subsequent step 102, the at least one first motion sensor may be operated so as to detect motion. For instance, the at least one first motion sensor may be embodied by one or more acceleration sensors.

At a step 104, parallel or time-displaced with respect to the step 100, a second motion sensor unit may be provided, the second motion sensor unit comprising at least one second motion sensor. Preferably the at least one second motion sensor is associated with, particularly mechanically linked to a second (or: maternal monitoring) transducer. The at least one second motion sensor may be applied to the abdominal region of the pregnant subject. The at least one second motion sensor may be associated with at least one maternal monitoring transducer that detects fetal medical condition information. At a subsequent step 106, the at least one second motion sensor may be operated so as to detect motion. For instance, the at least one second motion sensor may be embodied by one or more acceleration sensors. It is preferred that the at least one first motion sensor and the at least one second motion sensor are displaced (or: spaced apart) from each other when being applied to the abdominal region of the pregnant subject.

A step 108 may follow which comprises an evaluation of motion signals supplied by the at least one first motion sensor and the at least one second motion sensor. The step 108 may further include the determination of relative motion information indicative of relative motion between the at least one first motion sensor and the at least one second motion sensor. At a step 110, following the step 108, a decision or classification can be made indicating a level of relative motion. The step 110 may include a threshold-actual value comparison.

In case the actual relative motion level exceeds a defined threshold, the method may proceed with step 112, wherein a suppression mode is activated. When the actual relative motion level exceeds the defined threshold a strong indication may be given that a primary signal (also: main signal of interest) is most likely noise corrupted or, more specifically, motion corrupted, such that that further signal processing measures should be prevented. As used herein, the primary signal may involve fetal medical condition information and/or maternal medical information.

In case the actual relative motion level stays or falls below a defined threshold, the method may proceed with step 114, wherein an enablement mode is activated. When the actual relative motion level falls below the defined threshold a strong indication may be given that a primary signal (also: main signal of interest) is most likely basically undisturbed, such that that further signal processing measures may be permitted.

It goes without saying that the wording exceeding and falling below a defined threshold is presented above particularly for illustrative purposes, and not for limiting the scope if the disclosure. In other words, also a different mapping between exceeding/falling below and permission/prevention may be applied. The steps 108 to 114 may be repeated in a continuous or quasi-continuous manner, e.g. during a medical monitoring session.

Figure 6:
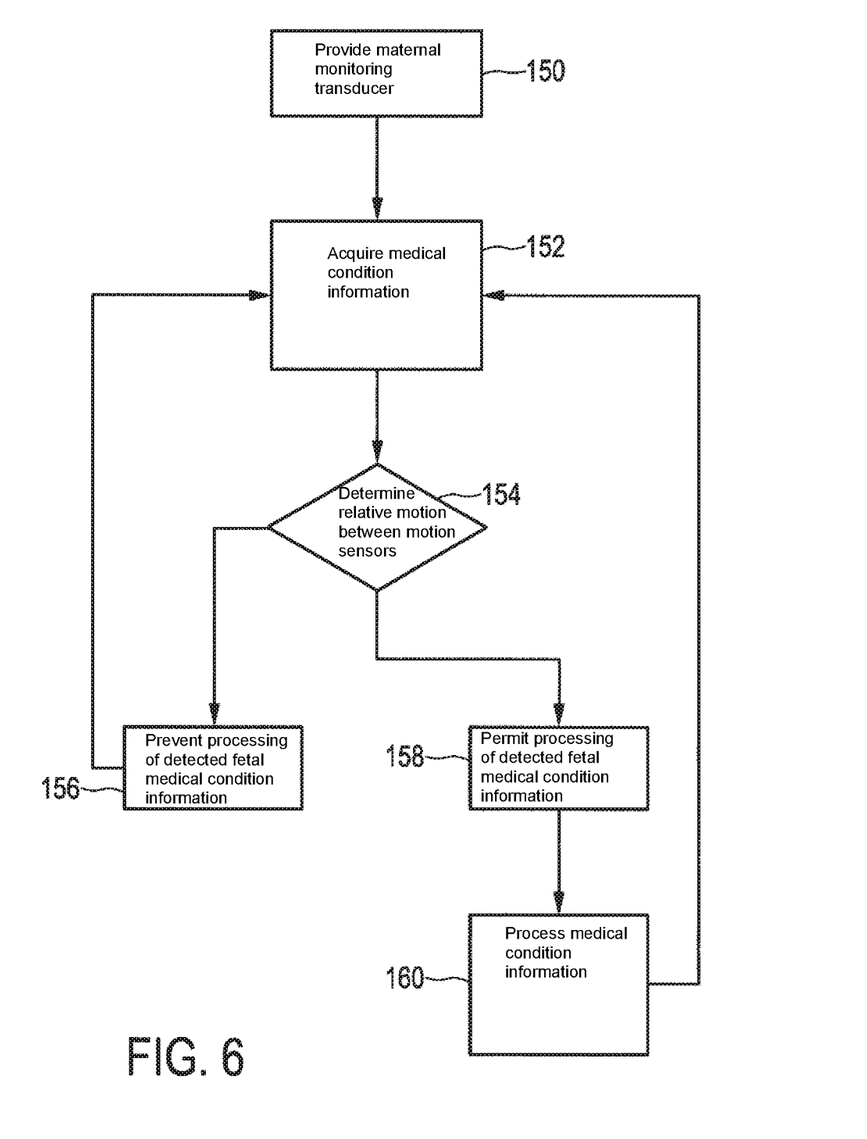
FIG. 6 shows an illustrative block diagram representing several steps of an alternative embodiment of a method in accordance with the present disclosure.

Further reference is made to FIG. 6 illustrating a method for detecting medical condition information from a pregnant subject. At a step 150, at least one medical condition monitoring transducer may be provided. The medical condition monitoring transducer may be embodied by a fetal monitoring transducer. In the alternative, the medical condition monitoring transducer may be embodied by a maternal monitoring transducer. Optionally, two medical condition monitoring transducers, e.g. a fetal monitoring transducer and a maternal monitoring transducer may be provided at step 150. At least one of the medical condition monitoring transducers, in some preferred embodiments each of the medical condition monitoring transducers, may be associated with at least one respective motion sensor, particularly with an accelerometer sensor or another suitable motion-sensing unit.

At a step 152, medical condition monitoring may be conducted, such that medical condition information is acquired or detect. Medical condition information may involve fetal heart rate information or fetal motion information in general, or maternal uterine contraction information or maternal motion information in general. It is emphasized in this regard that medical condition information as described above generally cannot be detected by any of the at least one respective motion sensor associated with the at least one condition monitoring transducer.

A further decision step 154 may follow which may include a status check. Step 154 may involve acquiring status information describing a level of relative motion between the at least one first motion sensor and the at least one second motion sensor. In other words, a flag signal indicating whether the suppression mode is to be applied (refer to step 112 in FIG. 5, for instance) or the enablement mode is to be applied (refer to step 114 in FIG. 5, for instance) may be received and used at step 154.

In case the status check performed at step 154 results in the suppression mode to be applied, a step 156 may follow which prevents processing of the detected fetal medical condition information. This may be at least in part due to an increased level of relative motion between the at least one first motion sensor and the at least one second motion sensor. Consequently, the detected medical condition information may be regarded as distorted.

In case the status check performed at step 154 results in the enablement mode to be applied, a step 158 may follow which permits processing of the detected fetal medical condition information. This may be at least in part due to a reduced level of relative motion between the at least one first motion sensor and the at least one second motion sensor. Consequently, the detected medical condition information may be regarded as undistorted. A step 160 may follow which includes further processing of the medical condition information.

Figure 7:
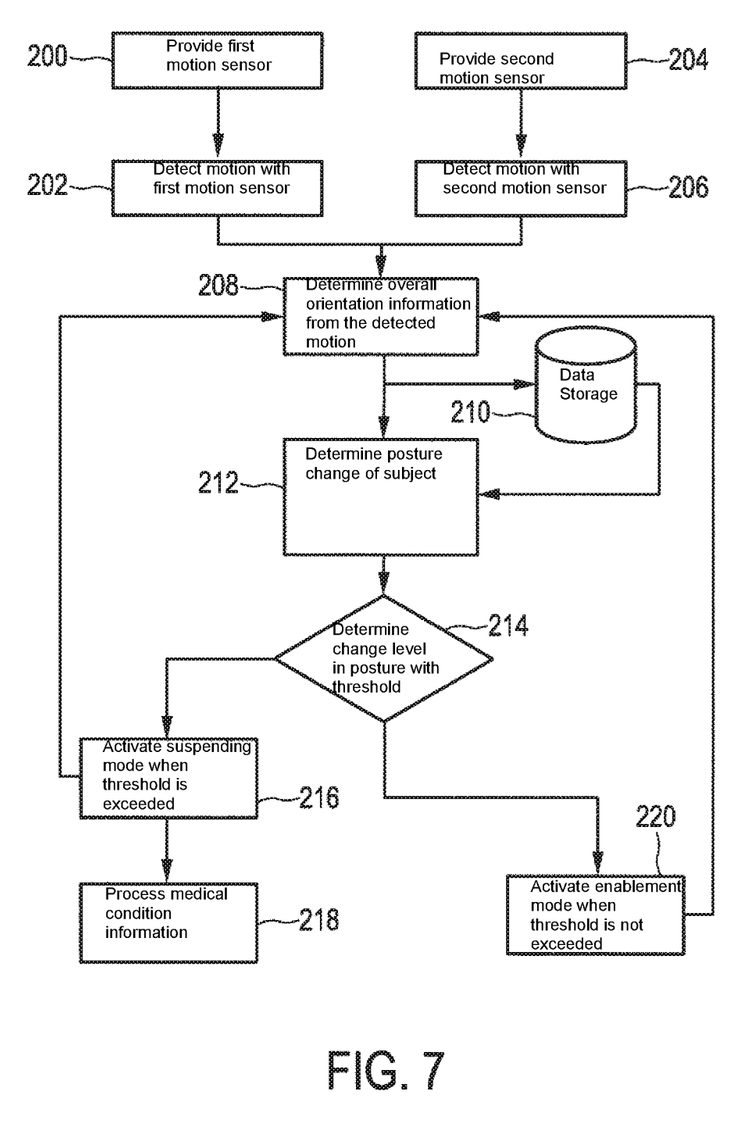
FIG. 7 shows an illustrative block diagram representing several steps of another alternative embodiment of a method in accordance with the present disclosure.

Further reference is made to FIG. 7 schematically illustrating a method for determining a change in posture in a monitoring system for an observed subject, particularly a pregnant subject, indicated by a change in overall orientation of the subject. The method described in connection with and illustrated in FIG. 7 may be combined with the method described in connection with and illustrated in FIG. 5. Particularly, the status information describing a level of relative motion between the at least one first motion sensor and the at least one second motion sensor may be used as a reference. When a level of relative motion between the first motion sensor unit and the second motion sensor unit indicates basically stable measurement conditions, the method as illustrated in FIG. 7 may be processed.

At a first step 200, a first motion sensor unit may be provided, the first motion sensor unit comprising at least one first motion sensor. Preferably, the at least one first motion sensor is associated with, particularly mechanically linked to a first (or: fetal monitoring) transducer. The at least one first motion sensor may be applied to an abdominal region of the pregnant subject. The at least one first motion sensor may be associated with at least one fetal monitoring transducer that detects fetal medical condition information. At a subsequent step 202, the at least one first motion sensor may be operated so as to detect motion. For instance, the at least one first motion sensor may be embodied by one or more acceleration sensors.

At a step 204, parallel or time-displaced with respect to the step 200, a second motion sensor unit may be provided, the second motion sensor unit comprising at least one second motion sensor. Preferably the at least one second motion sensor is associated with, particularly mechanically linked to a second (or: maternal monitoring) transducer. The at least one second motion sensor may be applied to the abdominal region of the pregnant subject. The at least one second motion sensor may be associated with at least one maternal monitoring transducer that detects fetal medical condition information. At a subsequent step 206, the at least one second motion sensor may be operated so as to detect motion. For instance, the at least one second motion sensor may be embodied by one or more acceleration sensors. It is preferred that the at least one first motion sensor and the at least one second motion sensor are displaced from each other when being applied to the abdominal region of the pregnant subject. The steps 202, 206 may cover a certain time span, e.g., a period of 1 second.

A step 208 may follow which comprises an overall orientation information determination step, particularly a posture detection step based on motion signals supplied by the at least one first motion sensor and the at least one second motion sensor. The step 208 may further include processing relative motion information indicative of relative motion between the at least one first motion sensor and the at least one second motion sensor. A subsequent step 212 may be directed to a determination of a change in posture of the observed subject. To this end, for instance, actual posture information supplied by the at least one first motion sensor and the at least one second motion sensor may be compared with reference posture information. It is therefore preferred that the change-in-posture determination step can make use of data provided in a data storage 210, wherein absolute and/or relative overall orientation information, e.g. posture information, is stored. It is emphasized in this regard that posture change detection may be directed at a detection of characteristic posture changes which might also induce a deferred posture change of the fetus.

As already set out above, at least in some embodiments, the detection of a general level of relative motion may be used to prevent further processing of medical condition information, when the level exceeds a certain threshold.

At a step 214, following the step 212, a decision or classification can be made indicating a level of a change in posture. The step 214 may include a threshold-actual value comparison. In case the actual change-in-posture level exceeds a defined threshold, the method may proceed with step 216, wherein a suspending mode is activated. In other words, when the pregnant mother-to-be experiences a certain change in posture, e.g. when turning and tossing, the fetus typically follows the general change in orientation with some time lag. When the actual relative motion level exceeds the defined threshold a strong indication may be given that a primary signal (also: main signal of interest) is most likely noise corrupted or, more specifically, motion corrupted, such that that further signal processing measures should be prevented. As used herein, the primary signal may involve fetal medical condition information and/or maternal medical information. At a step 218, following the suspension interval, finally, processing the medical condition information may be continued.

In case the actual posture change level stays or falls below a defined threshold, the method may proceed with step 220, wherein an enablement mode is activated. When the actual relative motion level falls below the defined threshold a strong indication may be given that a primary signal (also: main signal of interest) is most likely basically undisturbed, such that that further signal processing measures may be permitted.

It goes without saying that the wording exceeding and level falling below a defined threshold is presented above particularly for illustrative purposes, and not for limiting the scope if the disclosure. The steps 208 to 220 may be repeated in a continuous or quasi-continuous manner, e.g. during a medical monitoring session.

In the following, exemplary high-level algorithms are presented that can make use of several aspects of the disclosure as explained above. Particularly, the algorithms may be used when implementing a method in accordance with the present disclosure. The algorithm and the related method may suitably process data, or, more generally, signals provided by at least two motion sensor units.

Preferably, at least a first motion sensor of a first motion sensor unit is associated with a fetal monitoring transducer. Preferably, at least a second motion sensor of a second motion sensor unit is associated with a maternal monitoring transducer. Consequently, the sensors may be connected to their respective monitoring transducer. However, it may be sufficient in some applications that the motion sensors are arranged in the vicinity of their respective monitoring transducer. Consequently, as used herein, the term associated shall not be construed in a limiting way as requiring a mechanical link between the motion sensors and their respective monitoring transducers in any event.

Generally, the algorithms, related methods and systems are based on the insight that using multiple motion sensors, e.g. multiple accelerometers, may permit to detect and distinguish between maternal posture changes, undesired movements and orientation changes of the transducers. Consequently, a signal may be generated that selectively permits or prevents signal generation at the transducers and/or further processing of signals generated by the transducers. By way of example, fetal movement indication, or fetal heart rate indication may be suppressed when disturbing motion appearances have been detected. Generally, motion levels and orientations may be estimated over small time windows, e.g. in the range of one second. However, the movement pattern may be estimated over a longer time window. Therefore, the algorithms explained below may be repeatedly executed for respective time windows. Also moving time windows may be envisaged. Reference values used in any of the algorithms may be stored in respective buffers so as to enable a comparison between current and previous and/or predefined values.

Any algorithm may be composed of several subroutines which are set out below. For illustrative purposes, the maternal monitoring transducer will be referred to as tocodynamometer transducer hereinafter. For illustrative purposes, the fetal monitoring transducer will be referred to as ultrasound transducer hereinafter. For illustrative purposes, the at least one first motion sensor and the at least one second motion sensor will be referred to hereinafter as accelerometer for the ultrasound transducer, and as accelerometer for the tocodynamometer transducer, respectively. It may be further assumed, for the sake of simplicity, that the accelerometers are integrated and the respective transducers are integrated into a common housing.

A) Motion estimation subroutine for accelerometer integrated in housing of ultrasound transducer:

Compute motion level of accelerometer integrated in housing of ultrasound transducer and add it to a respective buffer. Apply motion level thresholding so as to obtain a binary motion level decision for the ultrasound transducer.

Compute orientation of ultrasound transducer accelerometer and add it to a respective buffer. Compare actual orientation with previous orientation(s) while also considering the computed motion level of the accelerometer integrated in housing of ultrasound transducer. Determine whether orientation of the ultrasound transducer accelerometer has changed so as to obtain a binary signal.

Determine an overall movement pattern for the accelerometer of the ultrasound transducer.

By way of example, the overall movement pattern may be composed of several motion-related parameters indicating movement direction, magnitude (or: distance), etc.

B) Motion estimation subroutine for accelerometer integrated in housing of tocodynamometer transducer:

Compute motion level of accelerometer integrated in housing of tocodynamometer transducer and add it to a respective buffer. Apply motion level thresholding so as to obtain a binary motion level decision for the tocodynamometer transducer.

Compute orientation of tocodynamometer transducer and add it to a respective buffer. Compare actual orientation with previous orientation(s) while also considering the computed motion level of the tocodynamometer transducer. Determine whether orientation of the tocodynamometer transducer accelerometer has changed so as to obtain a binary signal.

Determine an overall movement pattern for the accelerometer of the tocodynamometer transducer.

It may be further preferred that at least one motion sensor (or: accelerometer) is applied that is attached to a maternal abdominal region so as to provide basically independent reference data.

C) Motion estimation subroutine for accelerometer being applied to a maternal abdominal region:

Compute motion level of maternal abdominal region accelerometer and add it to a respective buffer. Apply motion level thresholding so as to obtain a binary motion level decision for the maternal abdominal region transducer.

Compute orientation of maternal abdominal region transducer and add it to a respective buffer. Compare actual orientation with previous orientation(s) while also considering the computed motion level of the maternal abdominal region transducer. Determine whether orientation of the maternal abdominal region transducer accelerometer has changed so as to obtain a binary signal.

Determine an overall movement pattern for the accelerometer applied to the maternal abdominal region.

D) Evaluation and motion estimation examples:

The above data acquired in addition to the data detected via the ultrasound transducer and/or the tocodynamometer transducer may be evaluated so as to further enhance monitoring accuracy and reliability. For instance, in a monitoring system an ultrasound transducer (generally, a fetal monitoring transducer) may be provided that is capable of detecting a signal that is indicative of fetal heart rate information. Further, more generally, the ultrasound transducer may be capable of detecting a signal that is indicative of fetal movement.

If only a subset of the accelerometers being used in the current arrangement, e.g., just one accelerometer, indicates that a change in orientation occurred, or that that a considerable level of motion occurred, it may be concluded that the involved accelerometer(s) are currently experiencing disturbing motion, e.g. due to operating errors. Consequently, actual processing and/or transferring of desired the medical condition information may be suppressed.

If each accelerometer being used in the current arrangement indicates that a change in orientation occurred, and that the respective overall movement pattern is basically similar, i.e., that the changes in orientation are consistent, it may be concluded that a "true" posture change occurred, rather than undesired movement of a single accelerometer due to mishandling, for instance. Consequently, a temporal guard interval may be activated for suppressing processing and/or transferring the medical condition information for a certain time frame.

If each accelerometer being used in the current arrangement indicates that motion occurred, and that the respective motion level is considerably high, i.e., that a motion threshold is exceeded, it may be concluded that "true" overall motion occurred, rather than undesired movement of a single accelerometer due to mishandling, for instance. Consequently, a temporal guard interval may be activated for suppressing processing and/or transferring the medical condition information for a certain time frame.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A pregnancy monitoring system, comprising:
 a fetal monitoring transducer attachable to a subject of interest and configured to detect fetal medical condition information;
 a first motion sensor unit associated with the fetal monitoring transducer, the first motion sensor unit comprising at least one first motion sensor, the fetal monitoring transducer and the first motion sensor unit being mounted in a common housing, wherein the at least one first motion sensor has a predefined orientation or location with respect to the fetal monitoring transducer;
 a second motion sensor unit comprising at least one second motion sensor; and
 a controller comprising an evaluator configured to determine a level of relative motion between the first motion sensor unit and the second motion sensor unit, wherein the determination of the level of relative motion is based on motion signals supplied by the at least one first motion sensor and the at least one second motion sensor and the level of relative motion indicates movement information of the at least one first motion sensor from the predefined orientation or location with respect to the fetal monitoring transducer;

wherein at least one of the at least one first motion sensor and the at least one second motion sensor is attachable to an abdominal region of the subject of interest;
wherein the controller activates a suppression mode when the level of relative motion between the first motion sensor unit and the second motion sensor unit exceeds a motion threshold, thereby indicating unstable measurement conditions for the fetal monitoring transducer;
wherein the controller activates an enablement mode when the level of relative motion between the first motion sensor unit and the second motion sensor unit stays or falls below the motion threshold, thereby indicating stable measurement conditions for the fetal monitoring transducer;
wherein the controller permits, in the enablement mode, processing of the detected fetal medical condition information; and
wherein the controller prevents, in the suppression mode, processing of the detected fetal medical condition information.

2. The pregnancy monitoring system as claimed in claim 1, wherein the fetal monitoring transducer is configured as an ultrasonic transducer configured to detect fetal heart rate indicative information or fetal movement indicative information.

3. The pregnancy monitoring system as claimed in claim 1, wherein at least one of the at least one first motion sensor and the at least one second motion sensor is an accelerometer sensor configured to detect acceleration indicative information.

4. The pregnancy monitoring system as claimed in claim 1, wherein the fetal monitoring transducer and the first motion sensor unit are mechanically linked to each other.

5. The pregnancy monitoring system as claimed in claim 1, wherein the first motion sensor unit and the second motion sensor unit are attachable, independently of each other, to the abdominal region of the subject of interest.

6. The pregnancy monitoring system as claimed in claim 1, wherein the controller suspends, in a suspension mode, processing of the detected fetal medical condition information after detecting a movement pattern indicating unstable measurement conditions, comprising a change in posture of the subject of interest.

7. The pregnancy monitoring system as claimed in claim 1, further comprising a maternal monitoring transducer configured to detect maternal medical condition information, wherein the second motion sensor unit is associated with the maternal monitoring transducer.

8. The pregnancy monitoring system as claimed in claim 7, wherein the maternal monitoring transducer is a pressure sensitive transducer configured to detect maternal uterine activity indicative information.

9. The pregnancy monitoring system as claimed in claim 1, wherein the evaluator further determines, on the basis of the determination of the level of relative motion, overall orientation information, and wherein the evaluator further determines a change in posture of the subject of interest indicated by a change in overall orientation of the subject of interest.

10. The pregnancy monitoring system as claimed in claim 9, wherein the evaluator is further configured to determine overall orientation information indicated by the level of relative motion between the at least one first motion sensor and the at least one second motion sensor.

11. The pregnancy monitoring system as claimed in claim 9, wherein the controller permits, in the enablement mode, processing of the overall orientation information, and wherein the controller prevents, in the suppression mode, processing of the overall orientation information.

12. A method for detecting medical condition information from a pregnant subject of interest, the method comprising:
determining a level of relative motion between a first motion sensor unit comprising at least one first motion sensor and a second motion sensor unit comprising at least one second motion sensor, wherein the determination of the level of relative motion is based on motion signals supplied by the at least one first motion sensor and the at least one second motion sensor and the level of relative motion indicates movement information of the at least one first motion sensor from a predefined orientation or location with respect to a fetal monitoring transducer;
activating a suppression mode when the level of relative motion between the first motion sensor unit and the second motion sensor unit exceeds a motion threshold, thereby indicating unstable measurement conditions for the fetal monitoring transducer;
activating an enablement mode when the level of relative motion between the first motion sensor unit and the second motion sensor unit stays at or falls below the motion threshold, thereby indicating stable measurement conditions for the fetal monitoring transducer;
permitting, in the enablement mode, processing of the fetal medical condition information detected by the fetal monitoring transducer associated with the first motion sensor unit; and
preventing, in the suppression mode, processing of the fetal medical condition information detected by the fetal monitoring transducer associated with the first motion sensor unit.

13. The method as claimed in claim 12, further comprising:
detecting maternal medical condition information with a maternal monitoring transducer, wherein the second motion sensor unit is associated with the maternal monitoring transducer.

14. The method as claimed in claim 12, further comprising:
determining, on the basis of the motion determination, overall orientation information;
permitting, in the enablement mode, processing of the overall orientation information;
preventing, in the suppression mode, processing of the overall orientation information;
determining a change in posture of the subject of interest indicated by a change in overall orientation of the subject of interest detected in the enablement mode; and
suspending, in a suspension mode, processing of the detected fetal medical condition information in response to a detection of a movement pattern indicating a change in posture of the subject of interest.

15. A non-transitory computer readable medium that stores therein a computer program product, which, when executed on a processor, causes the processor to carry out the method as claimed in claim 12.

16. A pregnancy monitoring system, comprising:
an ultrasound transducer attachable to a subject of interest and configured to detect fetal medical condition information;
a first motion sensor attached to the ultrasound transducer, the first motion sensor being different from the ultrasound transducer;

a second motion sensor that is attachable to an abdominal region of the subject of interest, the second motion sensor being different from the first motion sensor and being different from the ultrasound transducer;

at least one computer processor programmed to:

determine a level of relative motion between the first motion sensor and the second motion sensor from motion signals supplied by the first motion sensor and the second motion sensor, wherein the level of relative motion indicates movement information of the at least one first motion sensor from a predefined orientation or location with respect to the ultrasound transducer, activate a suppression mode when the level of relative motion between the first motion sensor and the second motion sensor exceeds a motion threshold, thereby indicating unstable measurement conditions for the ultrasound transducer, activate an enablement mode when the level of relative motion between the first motion sensor and the second motion sensor stays at or falls below the motion threshold, thereby indicating stable measurement conditions for the ultrasound transducer;

process, in the enablement mode, the detected fetal medical condition information; and not process, in the suppression mode, the detected fetal medical condition information.

17. The pregnancy monitoring system as claimed in claim 16, further comprising:

a maternal monitoring transducer configured to detect maternal medical condition information.

18. The pregnancy monitoring system as claimed in claim 16, wherein the at least one computer processor is programmed to suspend, in a suspension mode, processing of the detected fetal medical condition information after detecting a change in posture of the subject of interest.

19. The pregnancy monitoring system as claimed in claim 16, wherein the at least one computer processor is programmed to:

determine, on the basis of the motion determination, overall orientation information, and determine a change in posture of the subject of interest indicated by a change in overall orientation of the subject of interest.

20. The pregnancy monitoring system as claimed in claim 19, wherein the at least one computer processor is programmed to:

determine overall orientation information indicated by relative motion between the first motion sensor and the second motion sensor.

* * * * *